(12) United States Patent
Simpkins (10) Patent No.: US 7,575,567 B2
(45) Date of Patent: Aug. 18, 2009

(54) MULTIPLE MEDICATION IV PUMP

(76) Inventor: Dale H. Simpkins, 8 S. Lee St., Beverly Hills, FL (US) 34465

( * ) Notice: Subject to any disclaimer, the term of this patent is extended or adjusted under 35 U.S.C. 154(b) by 572 days.

(21) Appl. No.: 11/221,978

(22) Filed: Sep. 9, 2005

(65) Prior Publication Data

US 2006/0178619 A1    Aug. 10, 2006

Related U.S. Application Data

(60) Provisional application No. 60/647,798, filed on Jan. 31, 2005.

(51) Int. Cl.
*A61M 37/00* (2006.01)
(52) U.S. Cl. ........................................ 604/86
(58) Field of Classification Search ............... 604/65, 604/67, 246, 500, 890.1, 86; 222/252
See application file for complete search history.

(56) References Cited

U.S. PATENT DOCUMENTS

| | | | |
|---|---|---|---|
| 4,622,457 A * | 11/1986 | Bradley et al. ......... 235/462.14 |
| 4,865,584 A | 9/1989 | Epstein et al. | |
| 5,199,604 A | 4/1993 | Palmer et al. | |
| 5,431,627 A | 7/1995 | Pastrone et al. | |
| 5,531,697 A | 7/1996 | Olsen et al. | |
| 5,643,212 A | 7/1997 | Coutre et al. | |
| 5,651,775 A | 7/1997 | Walker et al. | |
| 5,681,285 A | 10/1997 | Ford et al. | |
| 6,070,761 A * | 6/2000 | Bloom et al. ................. 222/81 |
| 6,416,496 B1 | 7/2002 | Rogers et al. | |
| 6,519,569 B1 | 2/2003 | White et al. | |
| 2003/0139701 A1 | 7/2003 | White et al. | |
| 2004/0077996 A1 | 4/2004 | Jasperson et al. | |
| 2004/0104271 A1 | 6/2004 | Martucci et al. | |

FOREIGN PATENT DOCUMENTS

| | | |
|---|---|---|
| EP | 0 302 752 A2 | 8/1989 |
| EP | 0 473 240 A2 | 4/1992 |
| WO | WO 99/36112 A1 | 7/1999 |

OTHER PUBLICATIONS http://store.medicalresourceusa.com/infusion-pumps.html, 3 pages printed from Internet on Jul. 27, 2004.

* cited by examiner

*Primary Examiner*—Nicholas D Lucchesi
*Assistant Examiner*—Christopher D Koharski
(74) *Attorney, Agent, or Firm*—Richard C. Litman (57) ABSTRACT

The multiple medication IV pump provides automated intravenous delivery of one or more medications. A carousel assembly holds multiple medication vials, and a computerized control circuit operates the carousel to position a selected medication vial proximate to a spiking unit and mixing chamber to deliver the contents of the vial into an IV solution. The spiking unit and mixing chamber comprise a hollow chamber and a hollow spike, or needle, extending from the hollow chamber. The contents of a medication vial spiked onto the spiking unit flow into the mixing chamber. A fluid entry port located near the top of the mixing chamber is connected to a first pump such that a fluid may be pumped into the mixing chamber. A fluid exit port located near the bottom of the mixing chamber is connected to a second pump such that a fluid may be pumped out from the mixing chamber.

12 Claims, 12 Drawing Sheets

| STORED MEDICATION LIBRARY | | | |
|---|---|---|---|
| NAME | DOSAGE | DILUTION | INTERVAL |
| | | | |
| | | | |
| | | | |
| | | | |

MULTIPLE MEDICATION IV PUMP

REFERENCE TO RELATED APPLICATIONS

This application claims the benefit of priority from Provisional Application Ser. No. 60/647,798 filed Jan. 31, 2005.

BACKGROUND OF THE INVENTION

1. Field of the Invention

The present invention relates to an apparatus for delivery of intravenous medications. More particularly, the present invention is a multiple medication IV pump for automated delivery of a medication from one of several medication vials stored within the multiple medication IV pump.

2. Description of the Related Art

Intravenous (IV) delivery of fluids to a patient is commonplace in medical settings, ranging from the injection of a medication with a hypodermic syringe to the infusion of fluids, medications, and nutritional supplements by a pump. An IV infusion pump is typically used when it is necessary to give a fluid, such as a medication or a nutritional supplement, at a controlled rate over a relatively long time period. An IV line, or catheter, is placed into one of the patient's veins, and connected by a length of tubing to the IV infusion pump, which is, in turn, connected to an IV bag containing the fluid to be supplied.

In contrast to the controlled delivery of a fluid over a relatively long period of time, some medications are administered as a bolus injection, pushing a prescribed amount of the medication into the patient at once. A bolus injection may be made by injecting the medication, with a hypodermic syringe, directly into the patient's vein or body. Preferably, a medication is injected into an IV line that is placed in one of the patient's veins. Generally, administration of a medication into an IV line is followed by a flush of saline solution to ensure that all of the medication has been pushed into the patient. It is common to place an IV line for the purpose of administering bolus injections, such as when multiple intravenous injections may be required or a medication may need to be quickly administered intravenously, so that it is undesirable to spend time to locate a suitable vein for injection.

It is sometimes necessary to deliver multiple medications, or multiple doses of a single medication, over a relatively short time period. One example is in cardiac care, such as in response to a cardiac arrest. Advanced Cardiac Life Support protocols recommend various medications during the course of treating cardiac emergencies. In certain situations, bolus administration of a medication is repeated during the course of treatment until a desired outcome is achieved. In other situations, bolus administration of multiple medications may be given in sequence. In still other situations, bolus administration of one or more doses of one or more medications may be given along with, or followed by, a slow or drip infusion of a medication.

Automated delivery of a sequence of medications would save time, and could help to reduce mistakes in an emergency situation. While an IV pump is useful in delivering a medication, such pumps are typically limited to delivering a slow infusion of a single, or a limited number of, medications. While IV pumps are known to utilize multiple medication channels, and to employ a cartridge system allowing quick exchange or replacement of a medication-containing cartridge, the ability of an IV pump to load itself with a medication automatically from a self-contained medication supply, or to select proper medications for delivery according to a predefined protocol, is largely unknown.

Thus, a multiple medication IV pump solving the aforementioned problems is desired.

SUMMARY OF THE INVENTION

The multiple medication IV pump provides automated intravenous delivery of one or more medications. A carousel assembly within the multiple medication IV pump holds multiple medication vials, and a computerized control circuit operates the carousel to select a given medication, position the medication proximate to a spiking unit and mixing chamber, and deliver the contents of the medication vial into an IV solution stream.

The spiking unit and mixing chamber comprise a hollow chamber and a hollow spike, or needle, extending from the hollow chamber. The spike is adapted for insertion into a medication vial so that the contents of the medication vial flow into the mixing chamber. A fluid entry port located near the top of the mixing chamber is connected by a fluid conduit to a pump so that a fluid may be pumped into the mixing chamber. A fluid exit port located near the bottom of the mixing chamber is connected by a fluid conduit to a pump so that a fluid may be pumped out from the mixing chamber.

The carousel comprises a central hub, from which extends a plurality of track arms adapted to hold multiple medication vials. The carousel rotates to position a selected one of the track arms proximate to the spiking unit. Each track arm has a movable track disposed about the perimeter of the track arm, the track having a plurality of medication vial holders. As the track moves about the perimeter of the track arm, medication vials held in the medication vial holders are moved. Thus, by selecting a given track arm to be rotated into position proximate to the spiking unit, and then by rotating the track arm's track to position a medication vial holder in alignment above the spiking unit, a selected medication vial (or vial holder position) is brought into alignment with the spiking unit to allow delivery of the medication into the mixing chamber.

A vial-handling arm is associated with each track arm. Each vial-handling arm is adapted to grasp a medication vial from a vial holder of the track, and spike the medication vial onto the spiking unit. Each vial handling arm is further adapted to remove an empty vial from the spiking unit and to drop the vial for disposal.

A control circuit, including a display and keypad, allow for selection of a single medication, or a series or protocol of medications, to be automatically administered to a patient through an IV line in connection with the multiple medication IV pump.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1A:
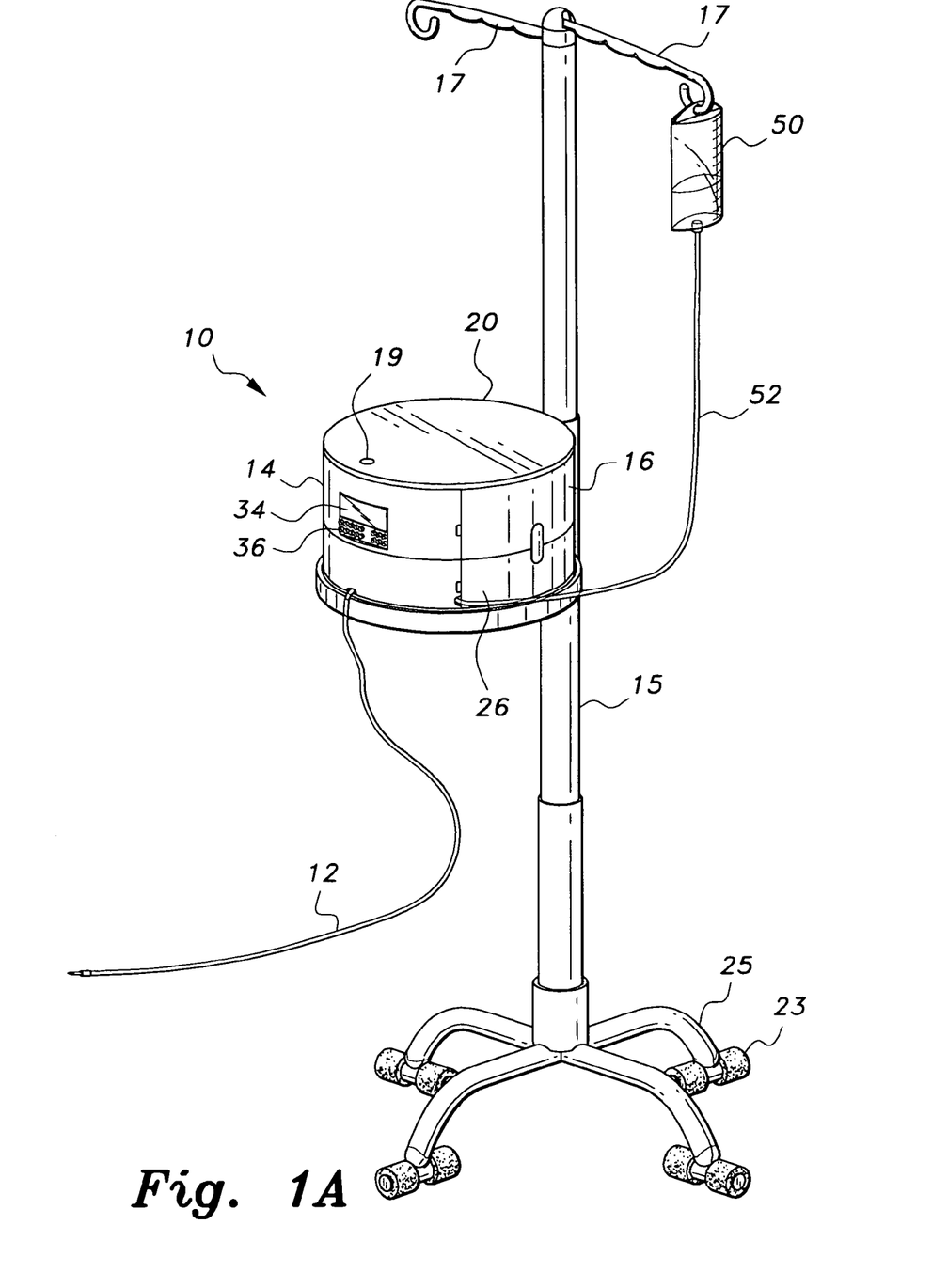
FIG. 1A is a perspective view of a multiple medication IV pump according to the present invention.
Figure 1B:
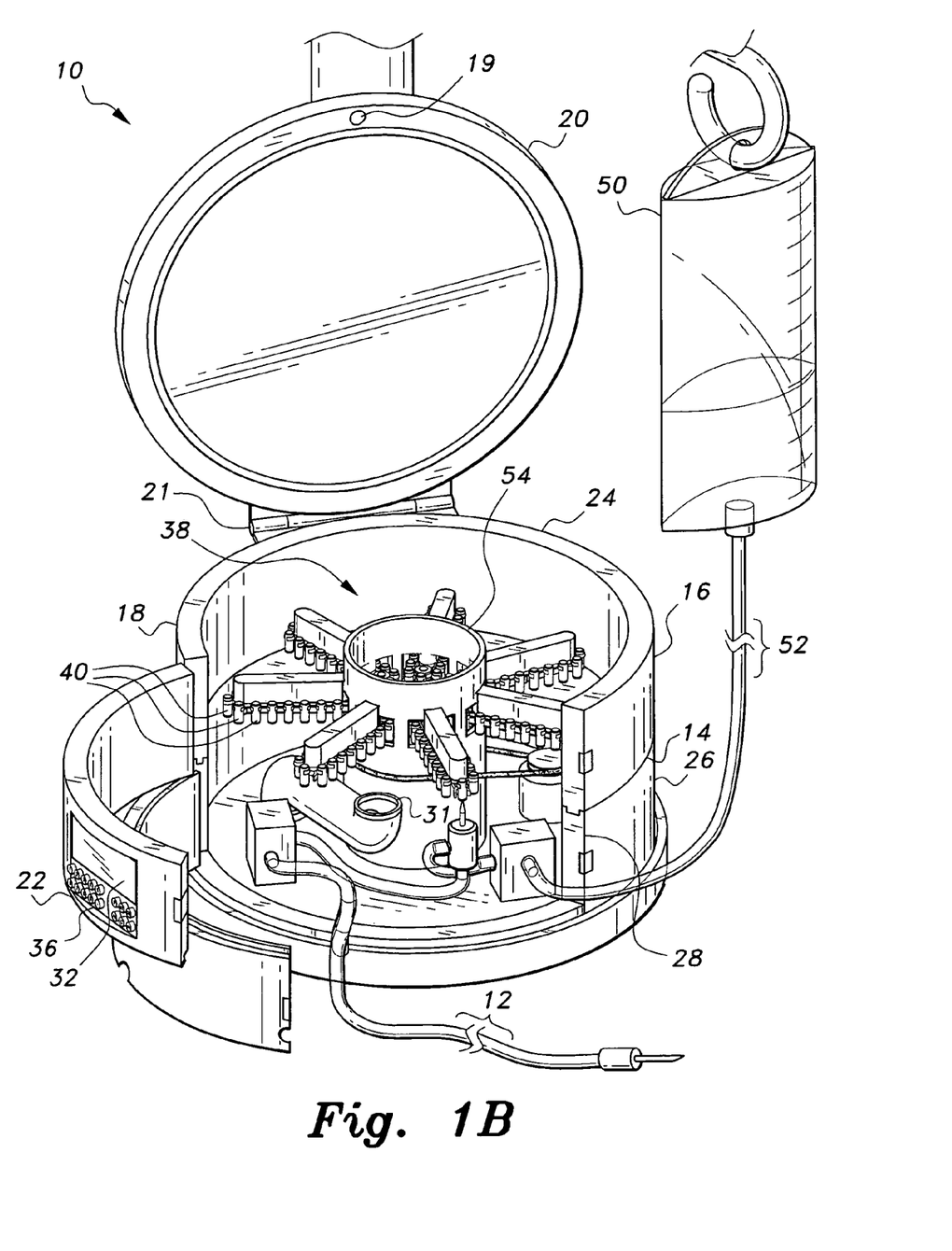
FIG. 1B is a perspective view of a multiple medication IV pump according to the present invention, opened to show an interior medication vial handling mechanism.
Figure 2:
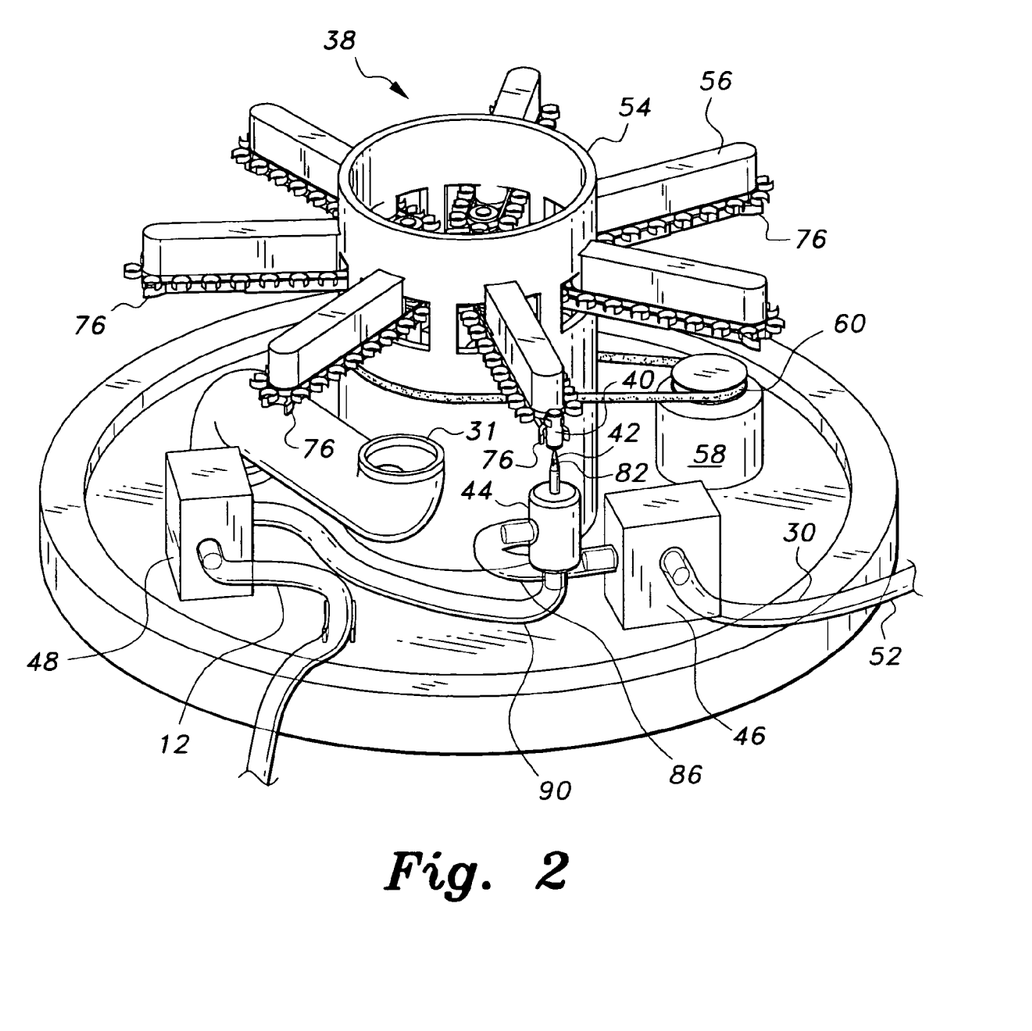
FIG. 2 is a perspective view of a medication carousel and a spiking unit and mixing chamber of a multiple medication IV pump according to an embodiment of the present invention.

The present invention is multiple medication IV pump, designated generally as 10 in the drawings. Referring to FIGS. 1A, 1B, and 2, the multiple medication IV pump 10 provides automated intravenous delivery of one or more bolus medications. Medication vials for multiple medications are contained within the multiple medication IV pump 10. A control circuit 32 allows a user to select a medication, or a series of medications, for intravenous delivery through an IV line 12 to a patient. The medications are delivered along with a fluid solution, such as a normal saline solution, used to flush the medication through the IV line 12, or to dilute the medication for correct administration.

The multiple medication IV pump 10 comprises an exterior housing 14 having a top shell 16 and a bottom shell 26. The top shell comprises a cylindrical outer wall 18 and a top 20, while the bottom shell 26 comprises a cylindrical outer wall 28 and a bottom 30. The cylindrical outer wall 18 of the top shell 16 comprises a hinged and movable front half 22 and a fixed rear half 24, so that the front half 22 may be opened for access into the interior of the housing 14. In the illustrated embodiment, the top shell 16 is removable from the bottom shell 26, and the top 20 of the top shell 16 is hinged, the top 20 being secured to the top shell 16 by a hinge 21. A lock 19 secures the top 20 in a closed position. A disposal chute 31 is disposed in the bottom shell 26 for removal of spent medication vials 40 through the bottom 30 of the housing 14. A receptacle may be located below an outlet of the disposal chute 31 for collection of the spent medication vials 40.

The multiple medication IV pump 10 is supported by a telescoping pole 15 mounted to the housing 14. The telescoping pole 15 has a plurality of legs 25 attached to the lower end of the pole 15. Coasters 23 may be provided at the ends of the legs to prevent the support legs from marring the floor or other supporting surface. A pair of horizontal support arms 17 is attached to the top of the telescoping support pole 15. Each support arm 17 is provided with a hook at the free end adapted for holding an IV bag 50. The support arms 17 are pivotally attached to the top of the telescoping pole 15 so that they can be rotated together in the horizontal plane to form a carrying handle for lifting the multiple medication IV pump 10 during transport.

The control circuit 32, comprising a display 34 and keypad 36, is disposed on the housing 14 for operation of the multiple medication IV pump 10 by a user. In the illustrated embodiment, the display 34 and keypad 36 are located on a front exterior surface of the bottom shell 26, although other configurations are suitable.

Within the housing 14 is a carousel assembly 38, adapted to hold a plurality of medication vials 40 or cartridges, and a spiking unit 42 and mixing chamber 44, adapted to receive a medication vial 40 and introduce the contents of the medication vial 40 into a fluid stream within the IV line 12. The carousel assembly 38, under control of the control circuit 32, positions a selected medication vial 40 in a position proximate to the spiking unit 42, and spikes the medication vial 40 onto the spiking unit 42 so that the contents of the medication vial 40 enter into the mixing chamber 44.

Figure 3:
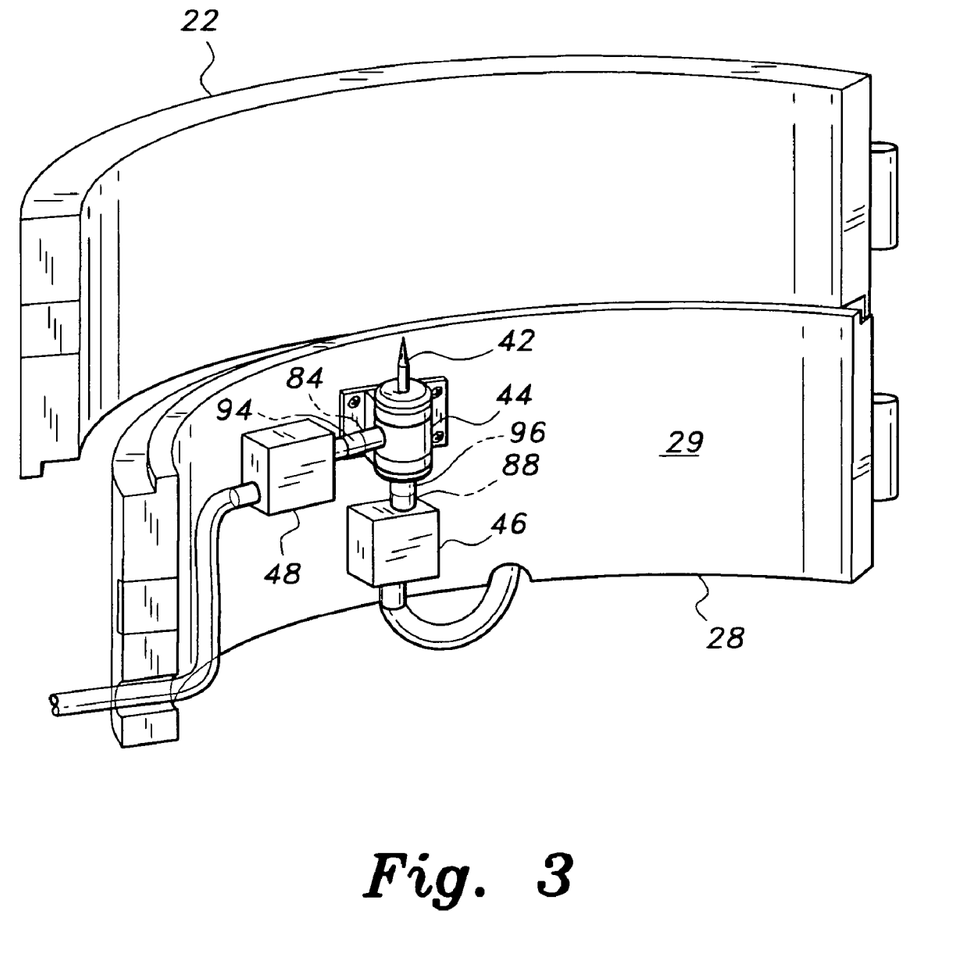
FIG. 3 is a perspective view of a pump, spiking unit, and mixing chamber assembly mounted on an inside wall of the multiple medication IV pump according to an embodiment of the present invention.
Figure 4:
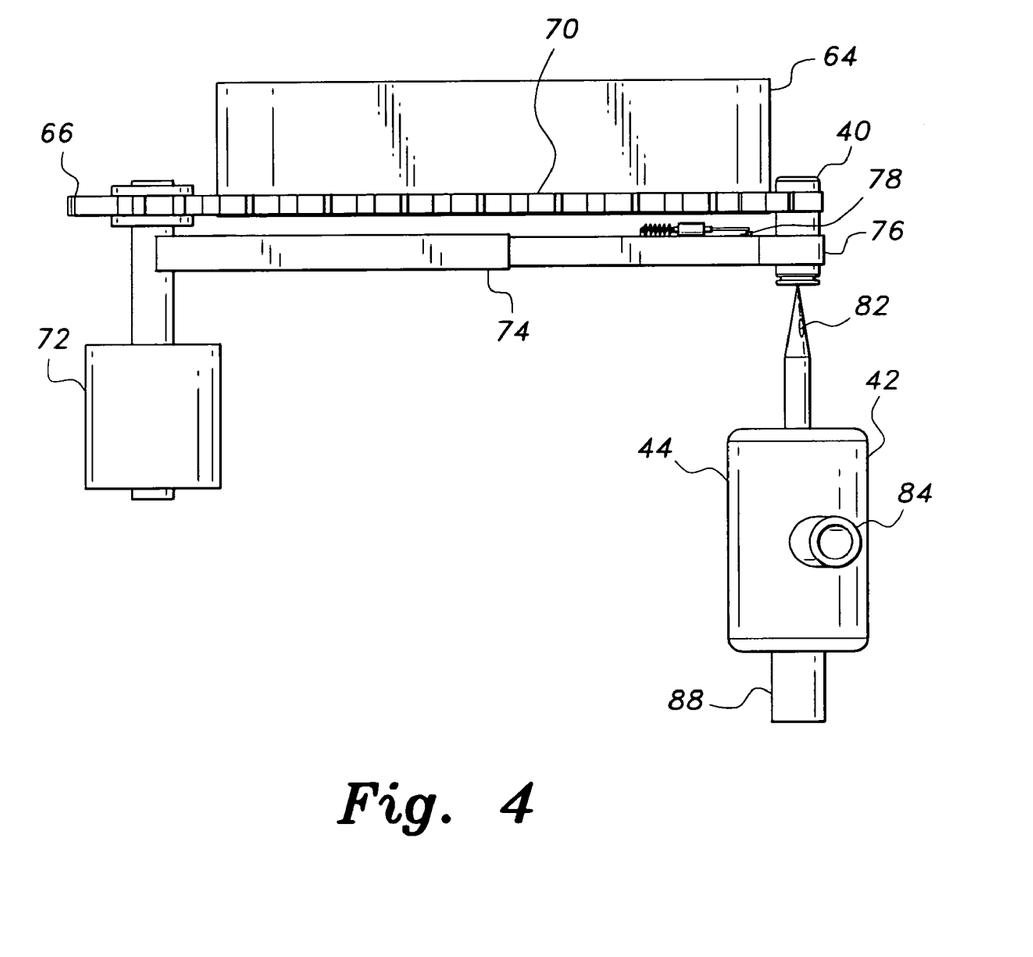
FIG. 4 is a side view of an arm assembly portion of the medication carousel shown in FIG. 2.

The spiking unit 42 and mixing chamber 44 allow for the introduction of a medication, from one of the medication vials 40, into a fluid stream for intravenous delivery to a patient. The multiple medication IV pump 10 has a first pump 46, located within the housing 14, that delivers a fluid, such as a normal saline solution, from an IV bag 50 or a similar source into the mixing chamber 44, via a length of IV tubing 52. A second pump 48, also located within the housing 14, pumps the fluid and a medication from the mixing chamber 44 through the IV line 12 to the patient. Each of the pumps 46, 48 is in electrical communication with, and is controlled by, the control circuit 32. Referring to FIG. 3, the pumps 46, 48 are shown alternatively mounted along with the spiking unit 42 and mixing chamber 44, on an inner surface 29 of the cylindrical outer wall 28. The pumps 46, 48 and the spiking unit 42 and mixing chamber 44 may be collected on a removable portion of the cylindrical outer wall 28, such as a hinged front panel portion, to allow for periodic removal and replacement of these components.

Returning to FIG. 2, the carousel assembly 38 of the illustrated embodiment comprises a rotating central hub 54 and a plurality of arm assemblies 56 extending radially from the hub 54. A hub motor 58 functions to rotate the central hub 54, under the control of the control circuit 32. The hub motor 58 may be engaged with the hub 54 in a direct-drive configuration, or by a drive train such as the belt drive 60 shown. The hub motor 58 may be a stepping motor or another type of motor adapted for accurate positional control, such that the hub 54 may be rotated into a precise position to bring an arm assembly 56 into alignment with the spiking unit 42. Alternatively, positional control of the hub 54 may be achieved by use of appropriate positional markers and sensors on or adjacent to the hub 54, the positional markers and sensors in communication with the control circuit 32.

Turning now to FIGS. 4, 5A, 5B, 6A, and 6B, each of the arm assemblies 56 comprises a medication vial track 62, having a track support member 64 and a movable track 66 surrounding the track support member 64. The track support member 64 is an elongated, oval arm having an outer perimeter 68. The movable track 66 is entrained about the outer perimeter 68 such that the movable track 66 is movable along the outer perimeter 68.

Figure 5A:
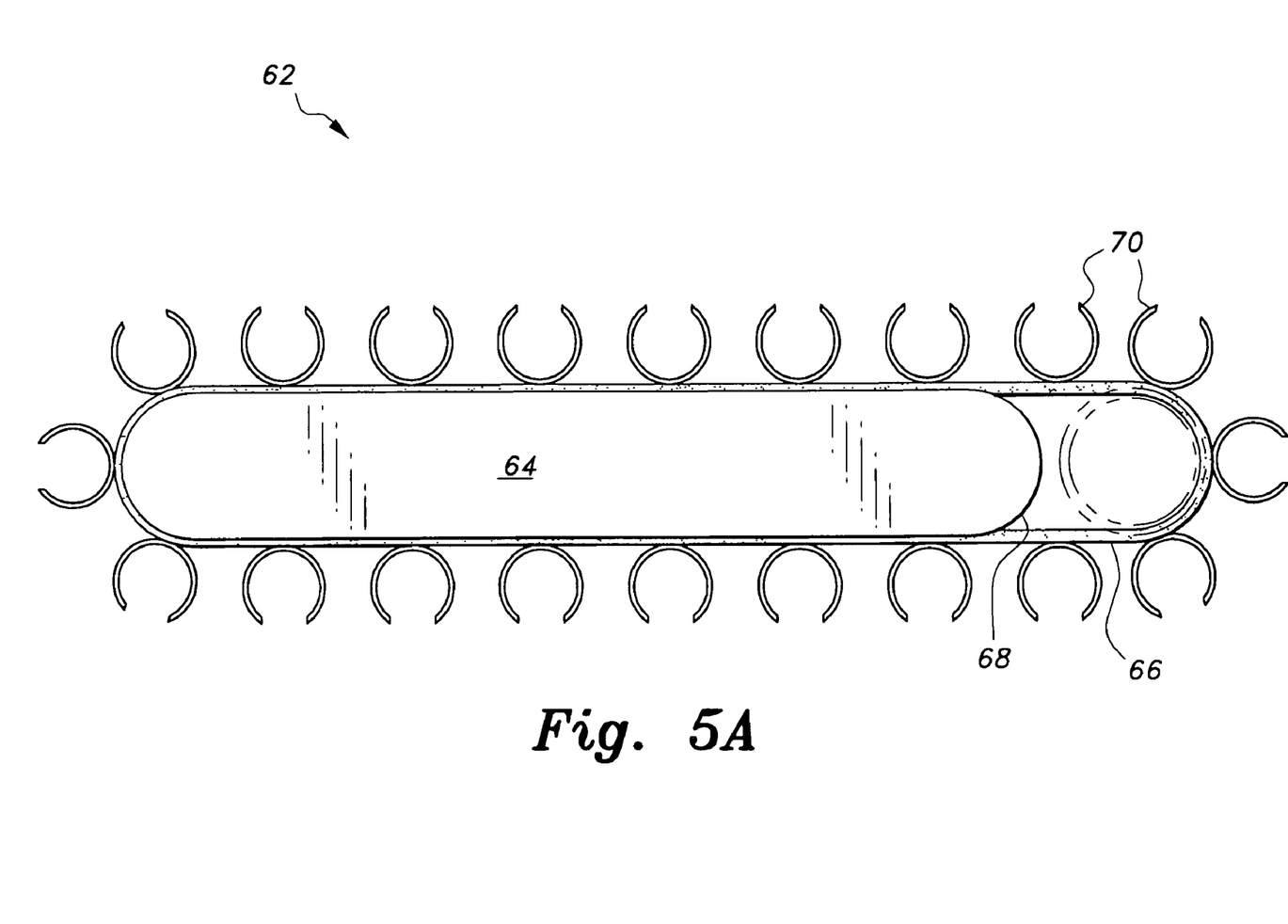
FIG. 5A is a top view of a medication vial track portion of the medication carousel shown in FIG. 2.
Figure 5B:
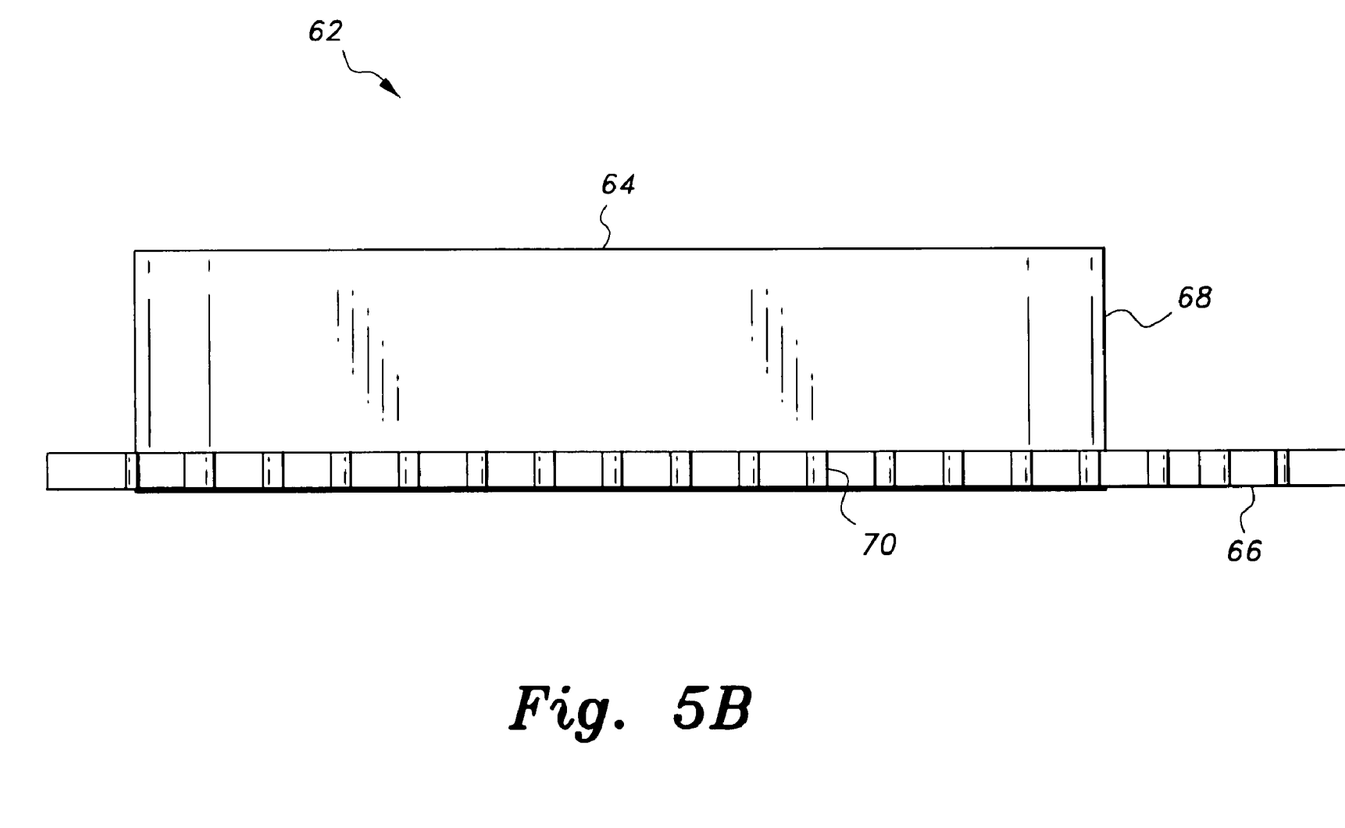
FIG. 5B is a side view of the medication vial track shown in FIG. 4.

A plurality of vial holders 70 are disposed along the movable track 66, each vial holder 70 being adapted to retain a medication vial 40. A track motor 72 is engaged to the movable track 66 to move the movable track 66 about the track support member 64. The track motor 72 may be a stepping motor or another type of motor adapted for accurate positional control, such that the movable track 66 may be positioned to bring a vial holder 70 into alignment with the spiking unit 42. Alternatively, positional control of the movable track 66 may be achieved by use of appropriate positional markers and sensors on or adjacent to the movable track 66 or the track support member 64, the positional markers and sensors in communication with the control circuit 32.

Figure 6A:
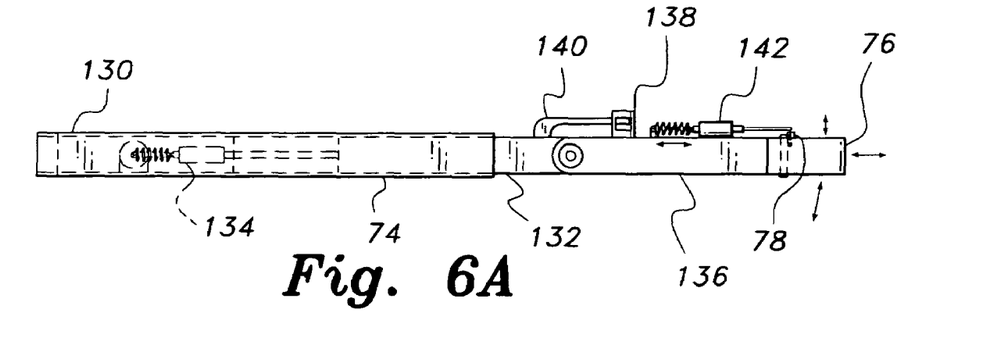
FIG. 6A is a side view of a vial handling arm portion of the medication carousel shown in FIG. 2.
Figure 6B:
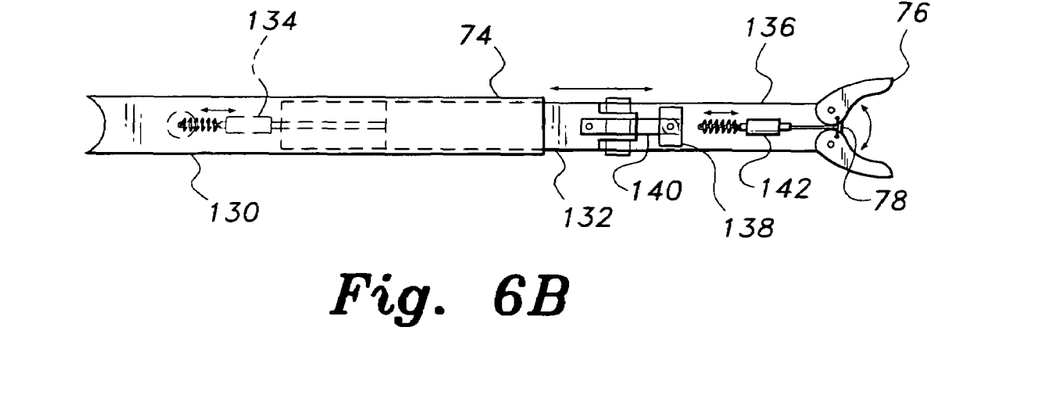
FIG. 6B is a top view of the vial handling arm shown in FIG. 6A.

In conjunction with the medication vial track 62, each of the arm assemblies 56 comprises a vial-handling arm 74. The vial-handling arm 74 comprises a fixed member 130, the fixed member 130 being generally a hollow tubular member. A telescoping member 132 slidably extends from the fixed member 130. A first actuator 134, such as a solenoid, is disposed within the fixed member 130 and connected to the telescoping member 132 such that the telescoping member 132 may be extended and retracted by the first actuator 134.

A vertically pivoting member 136 is pivotally attached to the telescoping member 132. A second actuator 138, such as a solenoid, is employed to move the vertically pivoting member 136 upward and downward. The second actuator 138 is disposed on the vertically pivoting member 136, and is connected to a lever arm 140 disposed on the telescoping member 132.

A vial grasping mechanism 76 is disposed on the vertically pivoting member 136, positioned to grasp a medication vial 40 from the medication vial track 62 in alignment with the spiking unit 42. A third actuator 142 is disposed on the vertically pivoting member 136, and is in connection with the vial grasping mechanism 76 to move the vial grasping mechanism 76 between an open and a closed position.

The second actuator 138 moves the vertically pivoting member 136 vertically such that a grasped medication vial 40 may be removed from the medication vial track 62 and spiked onto the spiking unit 42, and such that a medication vial 40 may be lifted from the spiking unit 42 for disposal, the vial grasping mechanism 76 dropping the medication vial 40 into the disposal chute 31. A barcode reader 78 is disposed on the vertically pivoting member 136 and oriented to read a barcode label on a medication vial 40 before removal of the medication vial 40 from the medication vial track 62.

Figure 7:
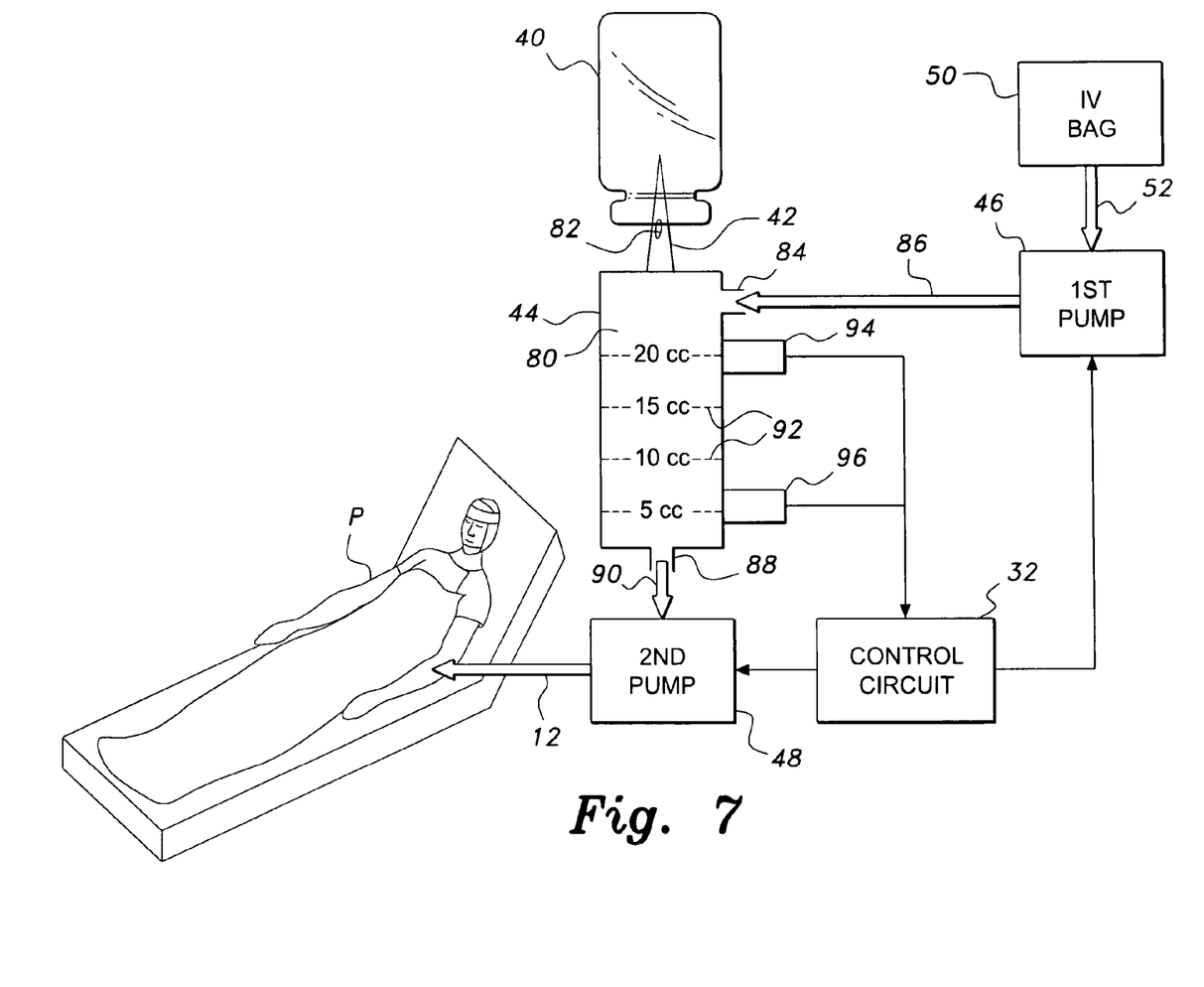
FIG. 7 is a block diagram of the spiking unit and medication chamber of the multiple medication IV pump according to the present invention.

Turning now to FIG. 7, the spiking unit 42 and mixing chamber 44 are illustrated in greater detail. The mixing chamber 44 comprises an enclosed receptacle having a hollow interior 80. The spiking unit 42 is essentially a hollow spike, or needle, extending from the mixing chamber 44, and in fluid communication with the hollow interior 80 of the mixing chamber 44. The spiking unit 42 is adapted for insertion into a medication vial 40 such that the contents of the medication vial flow into the hollow interior 80 of the mixing chamber 44. An aperture 82 formed along the length of the spiking unit allows entry of air into a spiked medication vial 40 to facilitate emptying of the contents of the medication vial 40 into the mixing chamber 44.

A fluid entry port 84 is located near the top of the mixing chamber 44. The fluid entry port 84 is connected, by a fluid conduit 86, to the first pump 46 so that a fluid may be pumped by the first pump 46 into the mixing chamber 44. In use, a fluid source, such as IV bag 50, is connected to the first pump 46 to supply fluid to the mixing chamber 44. A fluid exit port 88 is located near the bottom of the mixing chamber 44. The fluid exit port 88 is connected by a fluid conduit 90 to a second pump 48 so that a fluid may be pumped out from the mixing chamber 44. In use, the second pump 48 is connected to IV line 12 for delivery of the fluid and a medication to a patient P.

The hollow interior 80 of the mixing chamber 44 has a sufficient volume to contain a single, typical dose of a medication prepared for delivery to the patient. It should be noted that some medications will require dilution with a saline solution before delivery to the patient. Therefore, the volume of the hollow interior 80 of the mixing chamber 44 should accommodate a quantity of a fully diluted medication. In the illustrated embodiment, the volume is slightly greater than twenty cubic centimeters (20 CC). The mixing chamber 44 may be made of a transparent material, and may include visual volumetric indicia 92 disposed thereon for ready observation of the volume of fluid contained within the mixing chamber 44.

A pair of fluid level sensors provide control signals to the control circuit 32. A first level sensor 94 is located near the top of the mixing chamber 44 at a predefined volumetric level, such as at a twenty cubic centimeters (20 CC) level. The first level sensor 94 provides a signal to the control circuit 32 when the fluid level within the mixing chamber 44 rises above this level. A second level sensor 96 is located near the bottom of the mixing chamber 44 at a predefined volumetric level, such as at a five cubic centimeters (5 CC) level. The second level sensor 96 provides a signal to the control circuit 32 when the fluid level within the mixing chamber 44 falls below this level.

Figure 8:
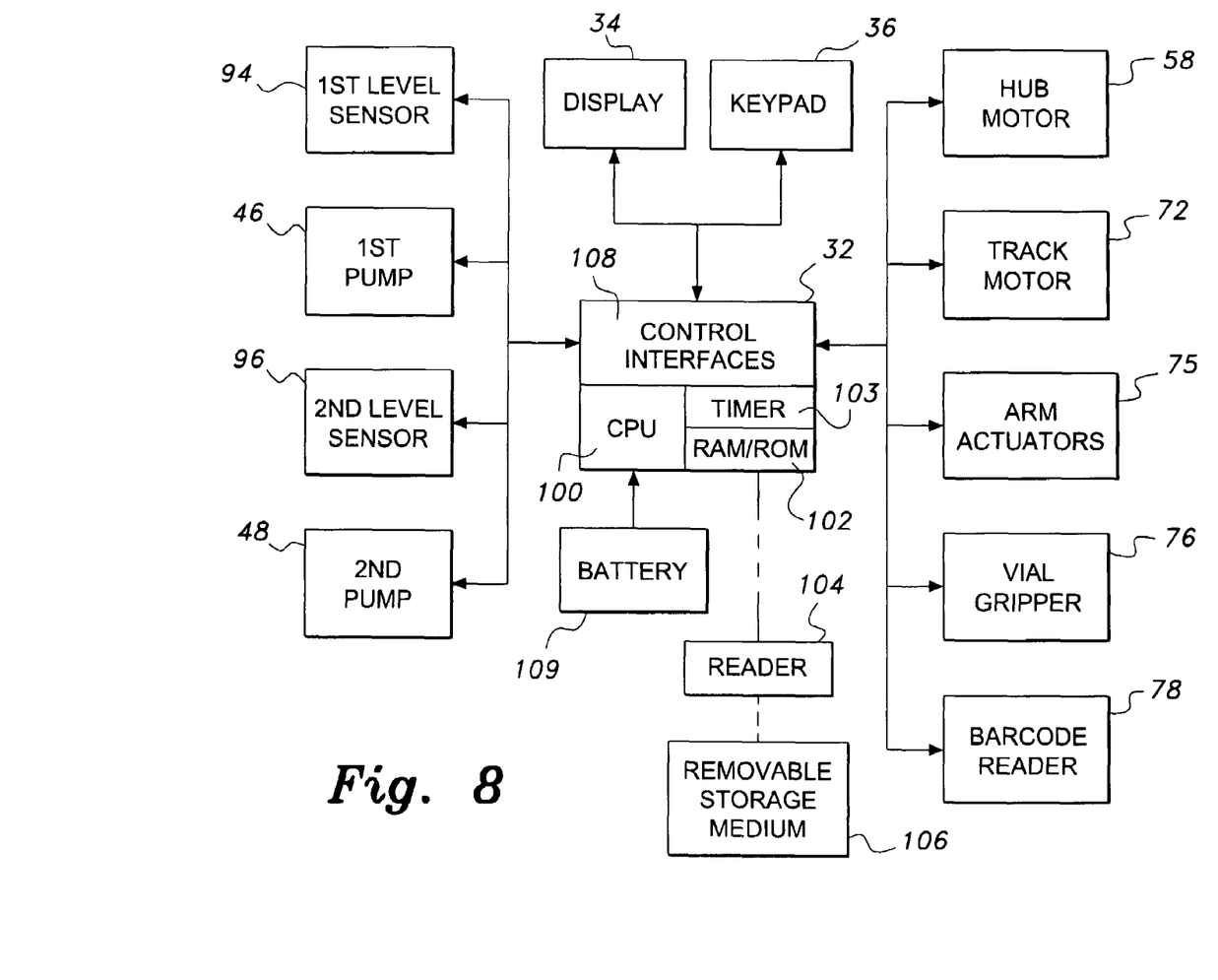
FIG. 8 is a block diagram of a control circuit for the multiple medication IV pump according to the present invention.

Turning now to FIG. 8, the control circuit 32 is discussed in greater detail. The control circuit 32 is, in the illustrated embodiment, a microcomputer based controller having a central processing unit (CPU) 100 in communication with a memory 102, the memory 102 including RAM and ROM memories. The CPU 100 is also in communication with a timer 103. Additionally, a reader 104 for a removable storage medium 106 may be provided in communication with the CPU 100. The control circuit 32 includes control interfaces 108 that communicate with the display 34 and keypad 36 to provide a user interface for the multiple medication IV pump 10. Additionally, the control interfaces 108 provide for connection to the hub motor 58, arm actuators 75, the vial grasping mechanism 76, the barcode reader 78, the first and second pumps 46, 48, and the first and second level sensors 94, 96. The control interfaces 108 provide for the operation of the first pump 46 and the second pump 48 at a variable speed such that the fluid volume and rates of the pumps 46, 48 may be controlled by the control circuit 32. A computer program stored in the memory 102 and executed by the CPU 100 operates the multiple medication IV pump 10. A battery 109 may be provided to power the control circuit 32.

Figure 9:
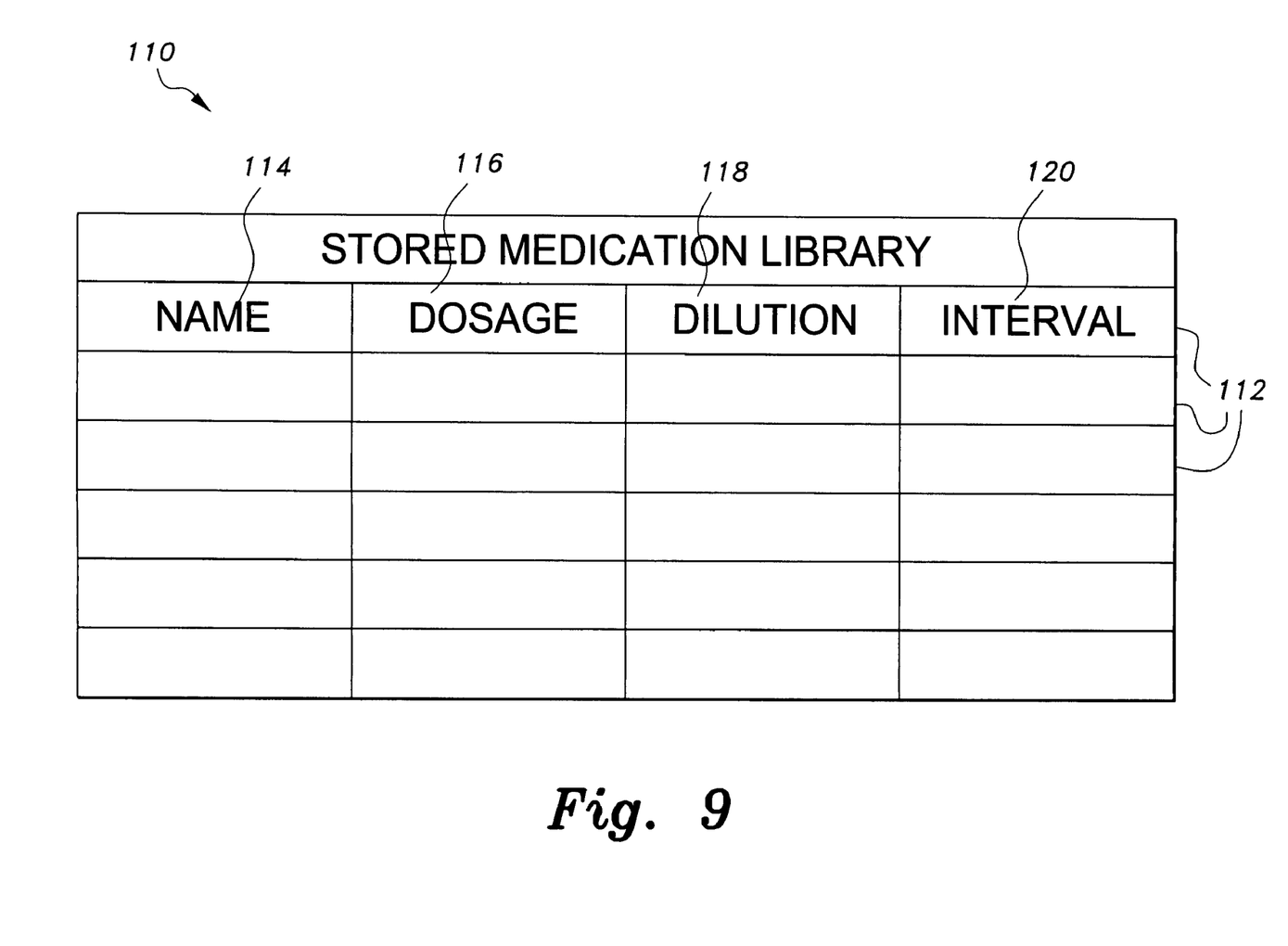
FIG. 9 is a block diagram of a stored medication library database for the multiple medication IV pump according to the present invention.

A stored medication library 110 is stored within the memory 102. Referring to FIG. 9, the stored medication library 110 is a database of the types of medications that will be used with the multiple medication IV pump 10. The stored medication library 110 includes an entry 112 for each of the medications that will be used with the multiple medication IV pump 10, each entry 102 including at least the name 114 of the medication, the dosage 116, a dilution factor 118 if the medication is to be diluted for use, and a repeat interval 120 if the medication is to be administered repeatedly. The stored medication library 110 may be stored in the ROM portion of the memory 102, or may be stored on a removable storage medium 106, the removable storage medium adapted for use with the reader 104, and loaded into the RAM portion of the memory 102. In addition to individual medication entries, the stored medication library 110 may include entries that indicate a medication protocol or series, wherein a medication protocol or series is simply a series of medications to be administered in a predetermined sequence and at predetermined dosages and intervals.

Figure 10:
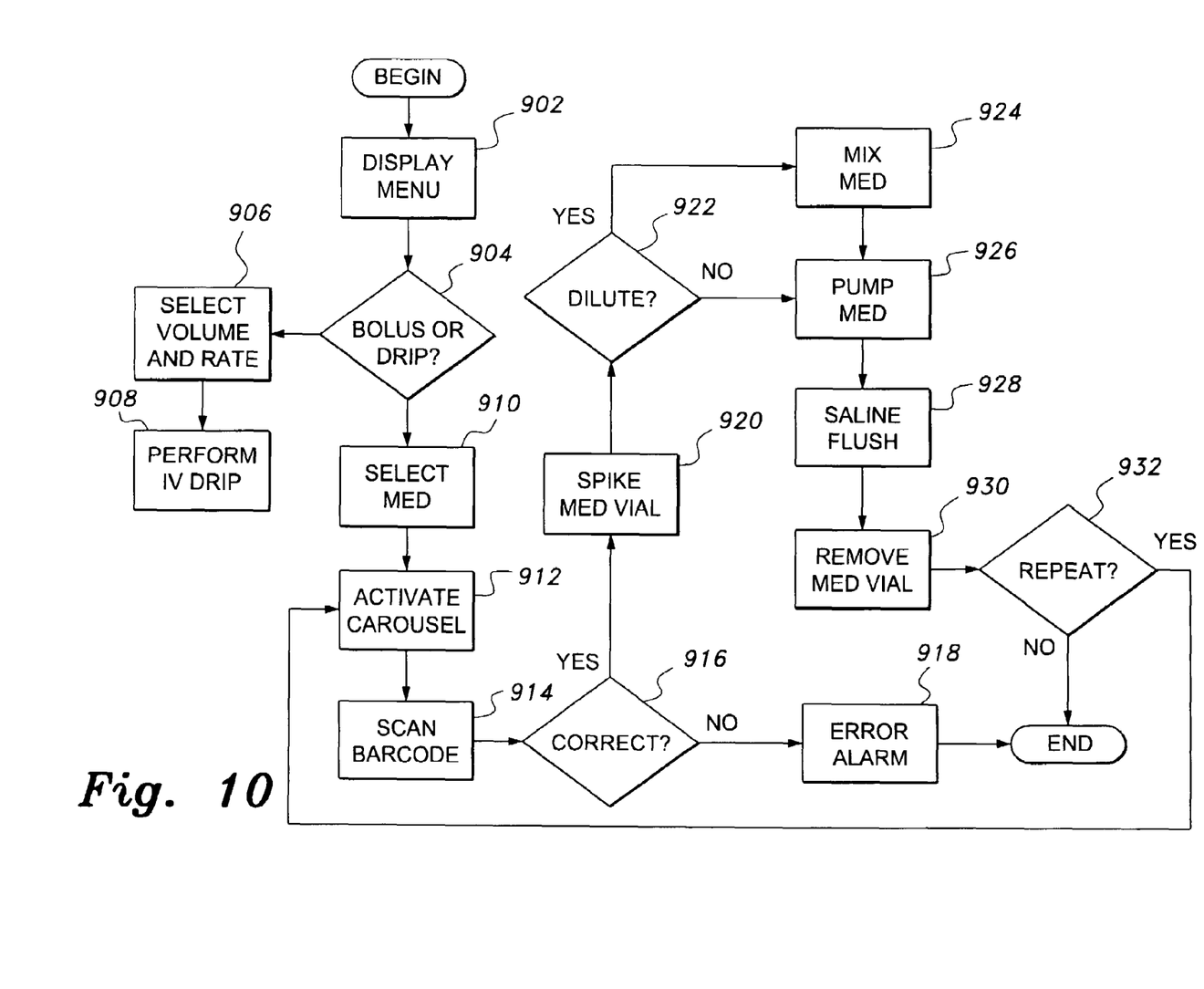
FIG. 10 is a flowchart describing the general operation of the multiple medication IV pump according to the present invention.

Turning now to FIG. 10, a typical operating sequence of the multiple medication IV pump 10 is described. The control circuit 32 displays a menu of selections on the display 34 (step 902). A user enters a selected operation using the keypad 36. Before operation of the multiple medication IV pump 10 to deliver a fluid or medication to a patient, the multiple medication IV pump 10 must be primed.

The priming steps (not shown) include attaching an IV bag 50 or other fluid source to the first pump 46, attaching an IV line 12 to the second pump 48, and operating the multiple medication IV pump 10 in a priming mode to ensure that the fluid from the IV bag 50 displaces all of the air in the system and the attached IV line 12. During the priming process, the fluid is pumped by the first pump 46 into the mixing chamber 44. Once the fluid level within the mixing chamber 44 reaches the second level sensor 96, the second pump 48 is activated to pump the fluid through the IV line 12. Once the fluid reaches the end of the IV line 12 (or after a sufficient time interval for the fluid to reach end of the IV line 12), both pumps 46,48 are turned off, leaving the multiple medication IV pump 10 primed with a small amount of the fluid remaining in the mixing chamber 44.

With the multiple medication IV pump 10 primed, the user selects the desired mode of operation. Initially, the user selects between a bolus mode and a drip mode (at 904). In the drip mode, used for ordinary infusion of IV fluids, the user enters a volume and rate for the infusion (step 906), and then the multiple medication IV pump 10 begins delivery of the IV drip by operating the first pump 46 and the second pump 48 together, controlling the speed of the pumps 46,48 to achieve the desired infusion rate (step 908). To deliver a medication bolus, the bolus mode is selected. A menu of available medications is displayed on the display 34, displaying the medications defined in the stored medication library 110. The user selects the desired medication (or a medication protocol) using the keypad (step 910). Note that a single medication may be selected, or a series or protocol of medications may be selected. In either case, the medication may be delivered according to default values contained within the stored medication library 110, or according to customized instructions that are entered when the medication or protocol is selected.

Once a medication has been selected, the medication name and information from the stored medication library is displayed on the display 34, along with information about the medication obtained from the stored medication library 110. If the medication is to be given repeatedly, an indication is displayed to remind the user. The medication may be repeated manually, at the initiation of the user, or automatically, at the initiation of the control circuit, according to the repeat interval 120 specified in the medication's entry 112 within the stored medication library 110.

Once a medication selection has been made, the carousel 38 is activated to position a medication vial 40 containing the desired medication in position at the spiking unit 42 (step 912). It can be noted at this point that the medication vials 40 can be placed into the carousel at predetermined and predefined positions so that a given medication is selected by the position of the carousel 38. Alternatively, although potentially slower, the medication vials 40 might be placed randomly within the carousel 38 and identified by the barcode reader 78 for use, the medication vials 40 being retrieved one at a time until the correct medication vial 40 is found. As an improvement to the random placement, the vials might be randomly placed, with the control circuit then performing a "learning" cycle wherein each of the medication vials 40 is scanned by the barcode reader for identification, and it's position then recorded.

Assuming that the medication vials 40 are stored in known positions, the control circuit 32 activates the hub motor 58 to rotate the carousel 38 so that an arm assembly 56 carrying the a medication vial 40 containing the desired medication is aligned with the spiking unit 42. The control circuit 32 then activates the track motor 72 of the arm assembly 56 to position a medication vial 40 containing the desired medication in alignment with the spiking unit 42.

The barcode reader 78 is then activated to read a barcode label on the medication vial 40 aligned over the spiking unit 42 (step 914). If the barcode label does not match the selected medication (at 916), an alarm is activated to bring attention to the error condition (step 918). If the medication vial 40 is correct, the vial handling arm 74 is activated to grasp the medication vial 40 and to spike the medication vial 40 onto the spiking unit 42 (step 920), releasing the contents of the medication vial 40 into the mixing chamber 44.

Some medications are to be delivered to the patient undiluted, while others must be diluted with saline solution (or another fluid) before delivery to the patient. The medication's entry 112 in the stored medication library 110 indicates whether or not the medication is to be diluted, as reflected by the dilution factor 118. If the medication is to be diluted (at 922), the first and second pumps 46, 48 are operated in sequence to dilute the medication within the mixing chamber before delivery to the patient (step 924). The medication is diluted by operating the first pump 46, with the second pump 48 off, to pump fluid into the mixing chamber 44. The first pump is operated by the control circuit 32 at a predetermined rate, and for a fixed time interval (measured by the timer 103), to pump an amount of fluid into the mixing chamber 44 to dilute the medication according to the dilution factor 118. Once the time interval has elapsed, and the correct amount of fluid is pumped into the mixing chamber 44, the second pump 48 is activated to deliver the diluted medication to the patient P, with both pumps 46, 48 operating as the medication is delivered (step 926).

If the medication is to be administered undiluted, the second pump 48 is activated simultaneously with the first pump 46, such that the undiluted medication is pumped to the patient P with both pumps 46, 48 operating as the medication is delivered (step 926). The first and second pumps 46, 48 continue operation for a sufficient time interval that a fluid flush follows the medication, to ensure that the entire dose of medication is delivered to the patient (step 928).

Once the delivery of the medication is completed, the vial handling arm 74 is activated to remove the medication vial 40 from the spiking unit 42 and to deposit the medication vial 44 into the disposal chute 31 (step 930).

A user programmed medication sequence, or a medication protocol contained within the stored medication library, or a particular medication dosage may require that the process be repeated with the same, or with a different, medication. If the cycle is to be repeated (at 932), the control circuit 32 repeats its operations from step 912, activating the carousel 38 to identify and load the next medication vial 40. Otherwise, the process is complete, returning to an initial menu display to await further user operations.

In the embodiment described above, the first and second pumps are described as being contained within the housing of the multiple medication IV pump. In another embodiment, one or both of first and second pumps may be external to the housing. The components of the pumps that come into contact with the medication of the fluids being pumped are selected so that they are chemically inert with respect to the medications being administered by the multiple medication IV pump. The pumps may be peristaltic pumps designed so that the pumped fluids come into contact only with tubing of the same type used for the IV lines.

It is to be understood that the present invention is not limited to the embodiment described above, but encompasses any and all embodiments within the scope of the following claims.

I claim:

1. A multiple medication IV pump, comprising:
a housing having an open interior;
a medication mixing chamber having a hollow interior, the chamber being disposed within said housing;
a spiking unit extending from the mixing chamber, the spiking unit being in fluid communication with the hollow interior of the chamber;
a motorized rotating carousel disposed within said housing, the carousel having a central hub and a plurality of elongated arm assemblies extending outwardly from the hub, each of the arm assemblies having a support member, a movable track surrounding the perimeter of the support member, and a plurality of vial holders disposed along the movable track and movable about the perimeter of said support member;
a microcomputer-based control circuit in electrical connection with the carousel and with the arm assemblies, the control circuit having a storage memory; and
computer readable program code stored within said memory, wherein execution of the program code operates the rotation of the carousel and the movement of the plurality of arm assemblies to bring a medication vial held in a selected one of said vial holders into fluid communication with the spiking unit.

2. The multiple medication IV pump according to claim 1, further comprising a first pump having a discharge port connected to said mixing chamber, said microcomputer-based control circuit being in electrical connection with said first pump, wherein execution of said computer readable program code controls the first pump to deliver a fluid into said mixing chamber.

3. The multiple medication IV pump according to claim 2, further comprising a second pump having an intake port connected to said mixing chamber, said microcomputer-based control circuit being in electrical connection with said second pump, wherein execution of said computer readable program code controls said second pump to transfer fluid from said mixing chamber.

4. The multiple medication IV pump according to claim 3, further comprising a user interface in electrical communication with said microcomputer-based control circuit, wherein execution of the computer readable program code specifies a medication protocol upon input from a user.

5. The multiple medication IV pump according to claim 4, wherein said medication protocol comprises a medication name, a dosage value, and a dosage interval.

6. The multiple medication IV pump according to claim 3, further comprising a database accessible by said microprocessor, the database having a plurality of medication entries; each of the medication entries including a medication name corresponding to a medication stored in one of the vial holders, wherein execution of said program code selects the vial holder holding the medication corresponding to each of the medication names.

7. The multiple medication IV pump according to claim 6, wherein said database further comprises a medication protocol entry; said medication protocol entry comprising a plurality of medication names, wherein execution of said program code selects a sequence of the vial holders holding medication corresponding to each of the plurality of medication names.

8. The multiple medication IV pump according to claim 6, wherein each medication entry further comprises a dilution value, wherein execution of said program code controls said first pump to transfer a volume of a diluting fluid into said mixing corresponding to said dilution value.

9. The multiple medication IV pump according to claim 6, wherein each medication entry further comprises a dosage value, wherein execution of said program code controls said second pump to transfer a volume of fluid from said mixing chamber corresponding to said dosage value.

10. The multiple medication IV pump according to claim 9, wherein each medication entry further comprises a repeat interval, wherein execution of said program code controls said second pump to repeatedly transfer a volume of fluid from said mixing chamber corresponding to said dosage value at intervals corresponding to said repeat interval.

11. An apparatus for administering a medication to a a patient, comprising:
a housing having an open interior;
a medication mixing chamber having a hollow interior, the chamber being disposed within said housing;
a spiking unit extending from said mixing chamber, the spiking unit being in fluid communication with said mixing chamber;
a motorized rotating carousel disposed within said housing, the carousel having a central hub and a plurality of elongated arm assemblies extending outwardly from the hub, each of the arm assemblies having a support member, a movable track surrounding the perimeter of the support member, and a plurality of vial holders disposed along the movable track and movable about the perimeter of said support member;
a first pump having a discharge port connected to said mixing chamber;
a second pump having an intake port connected to said mixing chamber;
a control circuit in electrical connection with the first and second pumps, the carousel and with the arm assemblies, wherein the control circuit controls the first pump to deliver a fluid into said mixing chamber and controls the second pump to transfer fluid from said mixing chamber, the control circuit further operating the rotation of the carousel and the movement of the plurality of arm assemblies to bring a medication vial held in a selected one of the vial holders into fluid communication with the spiking unit; and
a user interface provided within the control circuit for specifying a medication regimen.

12. The apparatus for administering a medication of claim 11, further comprising a bar code reader disposed within said housing, the bar code reader being electrically connected to said control circuit, said control circuit controlling the bar code reader to read an identifier on a medication vial held in a selected one of said vial holders and comparing said identifier to the name of a medication corresponding to a medication regimen selected using said user interface.

* * * * *